(12) United States Patent
Freiburger et al.

(10) Patent No.: US 10,575,825 B2
(45) Date of Patent: Mar. 3, 2020

(54) DOPPLER IMAGING

(71) Applicant: Siemens Medical Solutions USA, Inc., Malvern, PA (US)

(72) Inventors: Paul D. Freiburger, Seattle, WA (US); Mikyoung Park, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 899 days.

(21) Appl. No.: 14/809,564

(22) Filed: Jul. 27, 2015

(65) Prior Publication Data
US 2017/0027546 A1 Feb. 2, 2017

(51) Int. Cl.
*A61B 8/08* (2006.01)
*G01S 7/52* (2006.01)
*A61B 8/00* (2006.01)

(52) U.S. Cl.
CPC .............. *A61B 8/488* (2013.01); *A61B 8/461* (2013.01); *A61B 8/5207* (2013.01); *A61B 8/5269* (2013.01); *G01S 7/52066* (2013.01); *G01S 7/52077* (2013.01); *A61B 8/5253* (2013.01)

(58) Field of Classification Search
None
See application file for complete search history.

(56) References Cited

U.S. PATENT DOCUMENTS

| 4,485,821 A | 12/1984 | Iinuma |
| 4,561,019 A | 12/1985 | Lizzi et al. |
| 5,910,119 A | 6/1999 | Lin |
| 6,095,980 A | 8/2000 | Burns |
| 6,176,830 B1 | 1/2001 | Freiburger |

(Continued)

FOREIGN PATENT DOCUMENTS

| CN | 101404941 A | 4/2009 |
| CN | 102481142 A | 5/2012 |

(Continued)

OTHER PUBLICATIONS

Office Action dated Nov. 1, 2018 in corresponding Chinese Patent Application No. 201610852096.3.

(Continued)

*Primary Examiner* — Angela M Hoffa
*Assistant Examiner* — Farouk A Bruce

(57) ABSTRACT

To reduce speckle is spectral Doppler imaging, any oversampling relative to the velocity scale is used to create different data sets for the location at a given time. The different data sets have at least partially independent noise. Spectra are estimated from the different data sets and the resulting spectra combined into a spectrum with less speckle. To improve signal-to-noise ratio, the samples acquired for a given velocity scale are band-limited into different narrower bands. The portion of the spectrum estimated for each narrow band has a higher signal-to-noise ratio than a spectrum estimated for the entire band. The parts of the spectrum estimated for the different narrow bands are stitched together to provide a spectrum for the entire band with greater signal-to-noise ratio. In another approach, the user may input a narrow band relative to the velocity scale so that the corresponding part of the spectrum is provided with greater signal-to-noise ratio. Similar approaches may be used for color or flow imaging.

12 Claims, 7 Drawing Sheets

(56) References Cited

U.S. PATENT DOCUMENTS

| | | |
|---|---|---|
| 6,755,787 B2 | 6/2004 | Hossack et al. |
| 2003/0073894 A1 | 4/2003 | Chiang et al. |
| 2007/0161898 A1* | 7/2007 | Hao .................... G01S 15/8906 |
| | | 600/443 |
| 2007/0285315 A1 | 12/2007 | Davis et al. |
| 2009/0067699 A1 | 3/2009 | Clark |
| 2009/0088641 A1 | 4/2009 | Baba et al. |
| 2009/0149755 A1 | 6/2009 | Ann et al. |
| 2010/0022884 A1 | 1/2010 | Ustuner et al. |
| 2012/0089027 A1 | 4/2012 | Andreuccetti et al. |
| 2012/0256780 A1* | 10/2012 | Shoji ....................... G01S 13/18 |
| | | 342/101 |
| 2012/0283568 A1 | 11/2012 | Loftman et al. |
| 2012/0293359 A1* | 11/2012 | Fukuda ..................... G01S 3/48 |
| | | 342/107 |
| 2013/0041600 A1* | 2/2013 | Rick ....................... G01F 1/002 |
| | | 702/50 |
| 2013/0172749 A1 | 7/2013 | Lee et al. |
| 2014/0018680 A1* | 1/2014 | Guracar ................. A61B 8/463 |
| | | 600/440 |
| 2014/0051984 A1 | 2/2014 | Berger et al. |
| 2014/0066773 A1 | 3/2014 | Takimoto |
| 2015/0201904 A1 | 7/2015 | Guracar |
| 2015/0222838 A1 | 8/2015 | Kawabata et al. |
| 2016/0151038 A1 | 6/2016 | Anand et al. |

FOREIGN PATENT DOCUMENTS

| | | |
|---|---|---|
| CN | 103945771 A | 7/2014 |
| CN | 103494615 A | 8/2014 |
| CN | 104095656 A | 10/2014 |
| JP | H07-051270 | 2/1995 |
| JP | H08-000619 | 1/1996 |
| JP | H11-276477 | 10/1999 |
| JP | 3472604 B2 | 12/2003 |
| JP | 2007-082806 | 4/2007 |
| JP | 2007268298 A | 10/2007 |
| JP | 2009136680 A | 6/2009 |
| JP | 4365909 B2 | 11/2009 |
| JP | 2009-291325 | 12/2009 |
| JP | 5025400 B2 | 9/2012 |
| JP | 2013138866 A | 7/2013 |
| KR | 20140009058 A | 1/2014 |
| WO | WO2014045573 A1 | 3/2014 |
| WO | WO 2015011599 A1 | 1/2015 |

OTHER PUBLICATIONS

Korean Notice of Allowance dated Apr. 12, 2018 in corresponding Korean application No. 2016-0094559.

* cited by examiner

DOPPLER IMAGING

BACKGROUND

The present embodiments relate to Doppler ultrasound, such as color flow (e.g., flow mode) imaging or Doppler mode (e.g., spectral) imaging. By transmitting a plurality of pulses (e.g., pulsed wave (PW)) or a continuous wave (CW) at one more locations, a Doppler response is generated in response to received echo signals. For spectral Doppler, the frequency spectrum of the object's motion or flow for a single spatial region is estimated and displayed as a function of time. Spectral Doppler ultrasound imaging provides an image of spectra as velocity values (vertical axis) modulated by energy as a function of time (horizontal axis) for a gate location. The spectra may be used for studying fluid flow or tissue motion within a patient.

Spectral Doppler in medical ultrasound is limited in sensitivity due to electronic and acoustic noise and signal processing dynamic range. On difficult to scan patients, the signal-to-noise ratio is often insufficient to visualize the signal of interest, such as the maximum velocity of a cardiac jet or the presence of flow in a deep artery or vein. In other situations, the speckle noise degrades the image quality in the Doppler strip.

Other than using better quality electronic components and transducers, the noise may be reduced using image processing. For example, speckle noise is located in a Doppler strip and reduced. As another example, edges between noise and actual signal are found in the Doppler strip and enhanced. These processes use post-processing non-linear filters, but may not sufficiently increase the signal-to-noise ratio and/or reduce speckle.

BRIEF SUMMARY

By way of introduction, the preferred embodiments described below include methods, systems, computer readable media, and instructions for spectral Doppler imaging. To reduce speckle, any oversampling relative to the velocity scale is used to create different data sets for the location at a given time. The different data sets have at least partially independent noise. Spectra are estimated from the different data sets and the resulting spectra combined into a spectrum with less speckle. To improve signal-to-noise ratio, the samples acquired for a given velocity scale are band-limited into different narrower bands. The portion of the spectrum estimated for each narrow band has a higher signal-to-noise ratio than a spectrum estimated for the entire band. The parts of the spectrum estimated for the different narrow bands are stitched together to provide a spectrum for the entire band with greater signal-to-noise ratio. In another approach, the user may input a narrow band relative to the velocity scale so that the corresponding part of the spectrum is provided with greater signal-to-noise ratio. Similar approaches may be used for color or flow imaging.

In a first aspect, a method is provided for spectral Doppler imaging. An ultrasound system acquires samples representing a range gate location. The samples are oversampled relative to a velocity scale set for the spectral Doppler imaging. The samples are separated into two or more groups with each group of the samples satisfying a Nyquist criterion for the velocity scale. A Doppler estimator estimates two or more spectra for the Doppler gate location from the samples of the two or more groups, respectively. Information for the two or more spectra is combined into a combined spectrum. A spectral Doppler strip as a function of the combined spectrum is displayed.

In a second aspect, a method is provided for Doppler imaging. An ultrasound system acquires samples representing a location of a patient. The samples at least satisfy a Nyquist criterion for a velocity scale set for the Doppler imaging. A Doppler estimator estimates values for different ranges of frequencies within the velocity scale from the samples. The values are stitched together into a stitched value. A Doppler image is generated as a function of the stitched value.

In a third aspect, a method is provided for Doppler imaging. A velocity scale for the Doppler imaging is set as a first frequency range. A filter receives a user input of a second frequency range. The second frequency range is less than and within the first frequency range. The filter filters samples for a location of the patient with the second frequency range as a pass band. A Doppler estimator estimates Doppler data from the filtered samples. An image is generated as a function of an output of the estimating.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Image quality may be improved for Doppler imaging, such as spectral Doppler imaging or color imaging. For signal-to-noise improvement, the band width is reduced beyond what is normally done in Doppler signal processing.

Band-limiting to narrower than the user or system requested frequencies improves signal-to-noise ratio. Since narrowing the band may eliminate some signals of interest, the raw data is reprocessed (e.g., estimate spectrum or velocity) multiple times at different narrow bands to cover the entire spectrum. Multiple narrow bands of spectral data are processed separately and stitched together to form a Doppler display. In another approach, a user or an algorithm selects a narrower subset of frequencies for reprocessing to improve signal-to-noise ratio.

For speckle reduction in the imaging, excess bandwidth in the sampling is used. With an oversampled Doppler signal, decimating the data into multiple groups, processing each group independently, and then combining the multiple results into one Doppler display reduces speckle.

Any combination of user selected narrower band, stitching together spectra from different narrow bands, or using oversampling to reduce speckle may be used. Any one or combination of two or more of these techniques may be used in pulsed wave (PW) Doppler, continuous wave (CW) Doppler, PW Doppler tissue imaging (DTI), and/or color flow modes.

Figure 1:
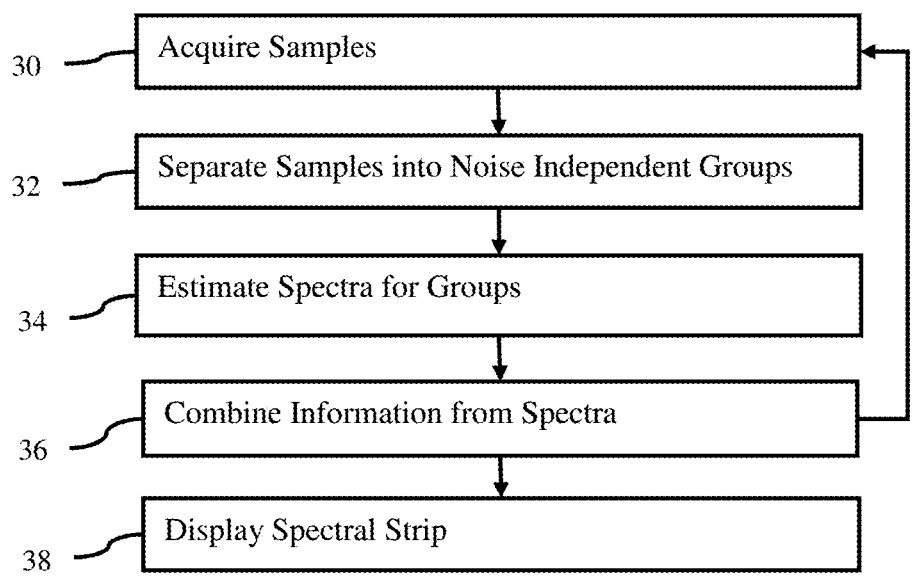
FIG. 1 is a flow chart diagram of one embodiment of a method for spectral Doppler imaging with reduced speckle.

FIG. 1 shows a method for spectral Doppler imaging with speckle reduction. Frequency compounding is provided. By using oversampling, different spectra are estimated for a same range gate representing the flow or motion at a same time. The samples are divided into two or more groups with at least partially independent noise. By combining information from the spectra estimated from the different groups, the speckle may be reduced.

The method is implemented for pulsed wave (PW) or continuous wave (CW) spectral Doppler. "Doppler" is used to express spectral processing in general, but may be used for color or flow modes. Other spectral processes using ultrasound samples from different times may be used. In PW, a gate location is sampled using pulse wave (e.g., 1-50 cycles) transmissions interleaved with echo reception. PW may interleave with other modes of imaging, such as B-mode or flow-mode. In CW, a continuous wave (e.g., hundreds or thousands of cycles) is transmitted to the gate location, and echoes are received while transmitting.

For spectral Doppler imaging, the sample gate or spectral Doppler gate is positioned. For example, a B-mode and/or flow-mode scan is performed. The user indicates a gate location on the resulting image. In other examples, the gate is automatically positioned, such as at a location of greatest Doppler velocity or energy determined from flow-mode data.

In other embodiments, the method is for color or flow mode imaging. Rather than processing by estimating spectra from each group, the different groups are used to estimate Doppler velocities (e.g., mean velocities). The resulting velocities from the different groups of samples are combined, resulting in reduced speckle for flow or color mode imaging of a region.

Figure 9:
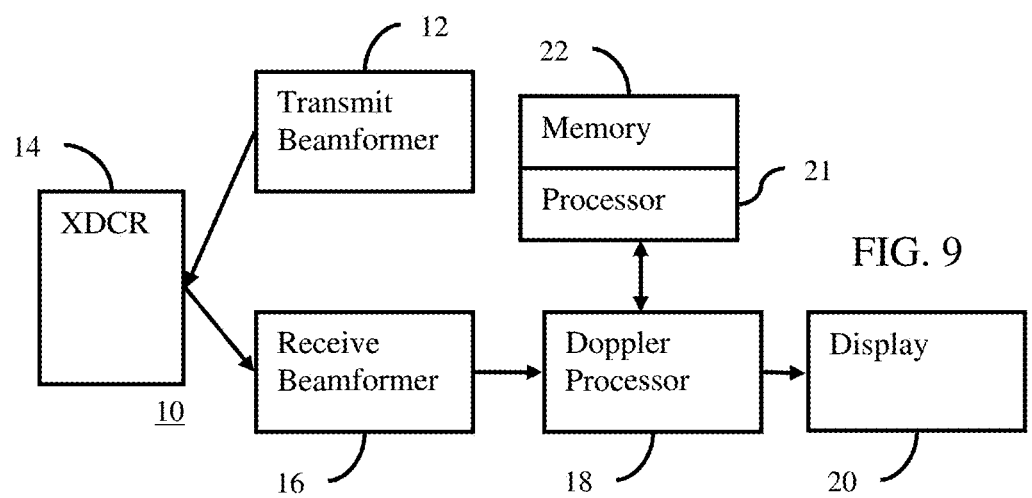
FIG. 9 is a block diagram of one embodiment of a system for Doppler imaging.

The method is implemented by the system 10 of FIG. 9 or a different system. The ultrasound system, such as a beamformer and transducer, acquire samples. A processor, such as a Doppler estimator, separates the samples, estimates spectra, and combines information from the spectra. The ultrasound system displays an image with reduced spectra based on the combination. A processor controls the acts. One or more acts may be performed through interaction with a user. Other acts or all the acts may be performed automatically by a processor without user input other than initial activation or gate location determination.

The acts are performed in the order shown, but other orders are possible. Additional, different, or fewer acts may be provided. For example, act 38 is not performed. In yet another example, acts for filtering, processing, maximum velocity determination over time, or other Doppler functions are provided.

In act 30, the ultrasound system acquires samples representing a range gate location. The samples are beamformed samples, but may be other raw data (e.g., channel data). In alternative embodiments, the samples are acquired by loading from memory or transfer from another device.

For acquisition by scanning, a transducer transmits a plurality of beams of acoustic energy. The acoustic or ultrasound energy of each transmission is focused at or near the gate location. A sequence of transmissions is performed. The repetition allows reception of sufficient samples to perform spectral or other Doppler analysis. Any number, such as 3-512, of transmit beams are transmitted so that a spectrum of the response from the Doppler gate may be estimated.

By performing additional transmissions, additional information is obtained for estimating spectra at other times. A given response to a given beam may be used for different spectra, such as where a moving window of received responses is used to generate each spectrum.

For speckle reduction, the samples are oversampled relative to a velocity scale set for the spectral Doppler imaging. The ultrasound system uses a velocity scale for the imaging. The velocity scale defines a range of frequencies over which the spectra or velocity is estimated and displayed. The velocity scale is selected or set to avoid aliasing in the estimation of the velocity of flow or motion. The velocity scale is selected by the user, a default or predetermined value of the system, and/or is adaptively determined by the ultrasound system.

Based on the velocity scale, the transmissions are performed at a pulse repetition frequency oversampling the motion or flow signal at the gate location. Any amount of oversampling may be used, such as an integer amount (e.g., M times the Nyquist rate for the velocity scale). Non-integer amounts of oversampling may be used.

In response to the transmissions, the transducer receives acoustic echoes. A receive beamformer samples the echoes to acquire received signals for the gate location. Receive beams are formed by focusing the received signals to coherently combine data representing the gate location. This combined data representing the gate location are beamformed signals or samples.

The receive operation occurs repetitively in response to the repetitive transmissions. Beamformed samples from the gate location at different times are received. Samples for the same location are acquired over time. For Doppler analysis, an ensemble of samples from a same location is acquired. The samples may be obtained in an ongoing manner such that a moving window (e.g., ensemble or flow sample count) with any step size (e.g., every sample or every third sample) is used to estimate a spectrum or velocity.

These responses (e.g., beamformed samples or channel data used for beamforming) are stored in a memory, such as a main memory, corner turning memory, or CINE. The responses to the Doppler transmissions are stored. This raw Doppler data prior to estimation is stored in an ongoing manner, such as storing the beamformed samples as acquired at a rate at the set or higher PRF.

The storage may be a first-in, first-out or other storage format. For example, the beamformed samples used to generate one or more spectra or velocities using multiple passes or estimations are stored. To use the same samples to estimate multiple spectra with the same Doppler estimator, the samples are stored to provide the processing in sequence. Alternatively, parallel processing is used so the samples are stored for less time. Where a moving window is used to estimate for different times, a given sample may be used in the estimations for different times. The samples are stored to account for this overlap. Alternatively, a greater or lesser number of responses are stored.

The samples are acquired for spectral Doppler processing. Typical spectral Doppler processing is to apply a Fast Fourier Transform (FFT) to the samples, providing a power spectrum for a given time. A display of the spectrum is generated by calculating a square root of the spectrum and log compressing the results. Other spectral Doppler processing may be used.

The oversampling may be used to improve the signal-to-noise ratio. Before application of the FFT, the samples are filtered with an anti-aliasing filter and decimated by any factor not violating the Nyquist criterion for the velocity scale. The filtering and decimation prior to estimation may result in the estimated spectrum having a higher signal-to-noise ratio.

Given the oversampled signal to start with where the signal-to-noise ratio is already acceptable (e.g., PW DTI), the extra oversampled bandwidth is used for speckle reduction or compounding instead of filtering and decimating to improve the signal-to-noise ratio.

In act 32, the samples are separated into two or more groups. The separation is by label, such as setting a flag for each memory location with samples. Alternatively, the samples of each group are copied to specific memory locations for the groups. In other alternatives, the separation is implemented by loading from designated memory locations as needed. Other separations may be used.

If the signal is oversampled M times, down-sampling may be used for speckle reduction. Due to oversampling, there are more samples than needed to satisfy the Nyquist criterion for the frequency range of the velocity scale. As a result, the samples may be separated into two or more groups of samples, where each group satisfies the Nyquist criterion. For example, M is 3, so three groups are formed where each group has sufficient samples to estimate a spectrum at the velocity scale. Since there are three groups, the samples for estimating three spectra for a same time are provided. Each group represents the response from the gate location at a same time.

Any separation format may be used. In one embodiment, the separation is interleaved. For example, every other sample is placed in one group where M=2. The remaining samples are placed in another group. For M=3, every third sample starting with sample 1 is placed in one group, every third sample starting with sample 2 is placed in another group, and every third sample starting with sample 3 is placed in yet another group. This interleaved format may be represented as sample@M*PRF being split into M groups: S(1:M:N−M+1), S(2:M:N−M+2), . . . , S(M:M:N), where N is the number of samples. Other formats may be used, such as interleaving sets of samples (e.g., samples 1 and 2, 7 and 8, . . . in one group where M=3).

Each sample to be used for a given time is in only one group after separation. In other embodiments, one or more samples may be positioned in multiple groups. Each group has a unique collection but may share one or more samples with other groups.

Where M is not an integer, excess samples may be discarded or not used. Alternatively, M is rounded down but the excess samples are placed into the M groups providing oversampling in each of the M groups.

By having each group of samples be unique, the groups represent an at least partially independent noise sampling. By having each sample used in only one group for a given time, the noise is sampled independently for each group. To provide this independence, the samples are not filtered across the samples prior to separation. A temporal, anti-aliasing, or clutter filter is not applied to the samples before separation. Any filtering, such as for band limiting in signal-to-noise enhancement, is applied to the samples of each group separately.

In act 34, a Doppler estimator estimates two or more spectra for the Doppler gate location from the samples of the two or more groups, respectively. M spectra are estimated from the M groups. Each spectrum has at least a partially independent representation of noise or speckle.

Each spectrum represents the energy as a function of frequency or velocity for a same time. Frequency has a known relationship to velocity, so expression in terms of frequency provides velocity and expression in terms of velocity provides frequency.

The Doppler estimator estimates the spectra from the responses or samples. Spectra are estimated for the Doppler gate location. The spectra are estimated by applying a Fourier transform, wavelet transform, or Wigner-Ville distribution to the sequence of ultrasound responses. Any transform may be applied to determine the spectra.

The spectra are estimated using the velocity scale. The signal from the fluid or tissue is over a range of positive and negative velocities. The range used in the estimation is the velocity scale. Any velocities beyond the velocity scale wrap around or are aliased. The spectra provide energy as a function of frequency over the range of frequencies set by the velocity scale.

The spectra are estimated from the ultrasound samples in the sequence of samples from the Doppler gate location. Each spectrum corresponds to a period in which the samples were acquired. The spectra estimated from the different groups represent a same time or the period.

In act 36, the Doppler estimator or other processor combines information for the two or more spectra into a combined spectrum. In one embodiment, the spectra representing the same location at a same time are summed. For each velocity or frequency, the corresponding energies are added. Alternatively, the spectra are averaged, which includes summing. The resulting spectrum may be filtered. Other combination functions of the spectra may be used, such as combination by peak detection.

In another embodiment, the separately estimated spectra are further processed separately, such as taking a square root, applying log or other compression, and mapping to display values. The combination occurs at any point along the process. For example, the pixel or display values from the different spectra for a given time are averaged. Each spectrum is mapped to a column of pixels to represent the spectrum of response for the gate location. Each pixel in the column is for a same time, but different velocity. The pixel value is mapped from the energy of the spectrum. Since this mapping occurs for each spectrum representing that time, an average of the display values for each pixel is calculated, providing a spectrum as display mapped. Other combinations at other points in the process may be used.

Figure 2A:
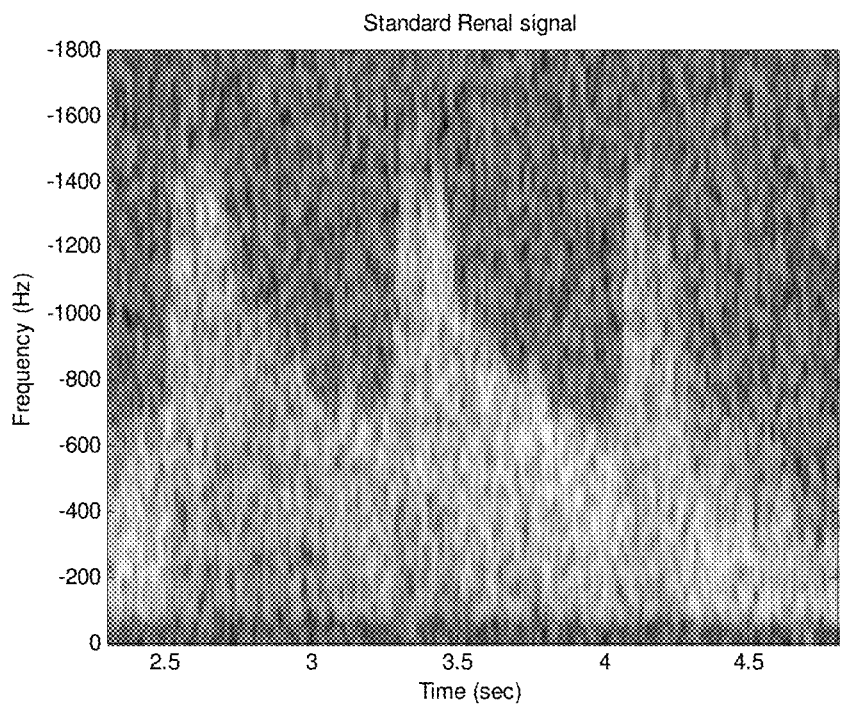
FIGS. 2A and B show example spectral strips without and with speckle reduction.
Figure 2B:
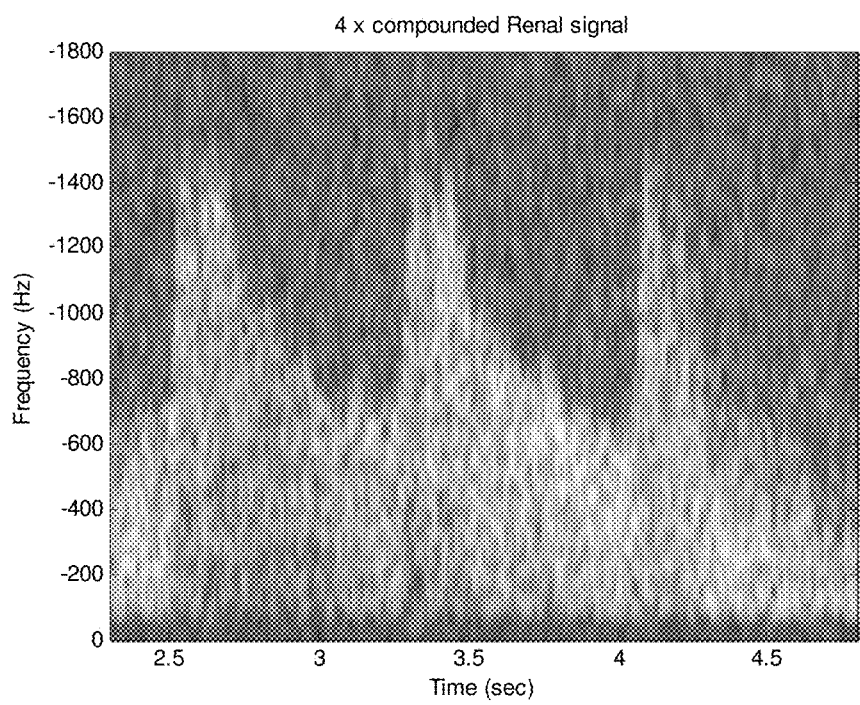

Acts 30, 32, 34, and 36 are repeated for different times. To create a spectral strip, a spectrum for each of different times is determined. FIGS. 2A and 2B shows spectral strips of spectra for a same location over time. The spectrum for a given time in a spectral strip is mapped with velocity on the horizontal axis and energy modulating the intensity. Other mapping may be used.

By repeating the acts, the spectra for the different times are acquired. As further samples are acquired, the further samples are added to the groups and old samples removed. A sequence of spectra for each group represents the Doppler gate location at different times. Other spectra may be estimated for other periods or different times corresponding to different periods or ensembles of acquisition. The periods may overlap, such as when using a moving window with a step size less than the ensemble period, or may be unique. The acquisition of samples and estimating for a different period are repeated to provide spectra over time. For a spectral strip, the process and corresponding repetition is on-going or occurs multiple times.

Each spectrum of the spectral strip is formed from multiple spectra. The oversampling is used to estimate more than one spectrum for each time, allowing combination that may reduce speckle.

In act 38, the processor or Doppler estimator generates an image on a display. The image is a function of the spectra, such as shown in FIGS. 2A and 2B. The spectrum or series of spectra may be used to generate a spectral strip. The spectral strip is displayed for the Doppler gate. Filtering may be applied to smooth the spectra along the time and/or frequency dimensions or over energy. The spectral strip shows the frequency modulated by energy as a function of time. Any now known or later developed spectral strip mapping may be used, such as gray scale mapping with the intensity representing energy. The energies modulate the pixels. The gray scale or color is mapped from the energy values. The displayed image may be a function of a single spectrum or of multiple spectra.

In one embodiment, the spectral strip is displayed with a spatial image, such as a one-dimensional M-mode, two-dimensional B-mode, two-dimensional F-mode (flow mode), or combination thereof image. The location of the gate may be indicated graphically in the image, such as represented by a circle in the region of interest of the field of view. For example, text, color, symbol, or other indicator shows the location for the range gate corresponding to the spectral strip. Alternatively, the spectral strip is displayed without imaging from another mode.

The spectral strip of the image includes the one or more spectra estimated with the velocity scale. The velocity scale defines a vertical range on the spectral strip. As additional samples are acquired, the resulting spectra for different times are added to the spectral strip, such as adding the spectra to a right side of the strip, shifting the remaining spectra one temporal step to the left, and removing the leftmost spectral strip. Each added spectrum is from a combination of information for spectra from the different groups. Other update or scrolling of the spectral strip may be used.

By combining the information from multiple spectra for each time, the amount of speckle in the spectral strip may be reduced. Given at least partial independent noise, the noise, including speckle, may cancel or be reduced in variation. FIG. 2A shows a spectral strip for a range gate location at a renal location. The spectral strip is generated without separating the samples, so without the speckle reduction. FIG. 2B shows the spectral strip generated from the same samples as FIG. 2A, but with the separation of samples where M=4. By combining the spectra for each time from the four groups, the amount of speckle in the spectral strip is reduced.

The embodiment discussed above for FIG. 1 is a spectral Doppler mode of imaging. The acts may be performed for Doppler flow or color mode in other embodiments. For estimating the velocity (e.g., mean Doppler velocity) for each location in a one, two, or three-dimensional region at a given period or time, a flow sample count (i.e., set of samples) is acquired. By oversampling, different estimates of velocity for a given location may be performed. Information from the different estimates is combined, such as by averaging. The resulting color or flow mode image may have less speckle.

In other embodiments, the oversampling is used for both speckle reduction and signal-to-noise ratio increase. Some of the extra bandwidth available due to oversampling is used to form separate groups for estimation of spectra and combining resulting information in speckle reduction. The samples in each group are assigned as oversampled themselves, allowing decimation prior to applying the Fourier transform to estimate the spectra. The resulting spectra have greater signal-to-noise ratio. The down-sampling with a prior group-based anti-aliasing filter may increase the signal-to-noise ratio in the spectra for the separated groups.

Figure 3:
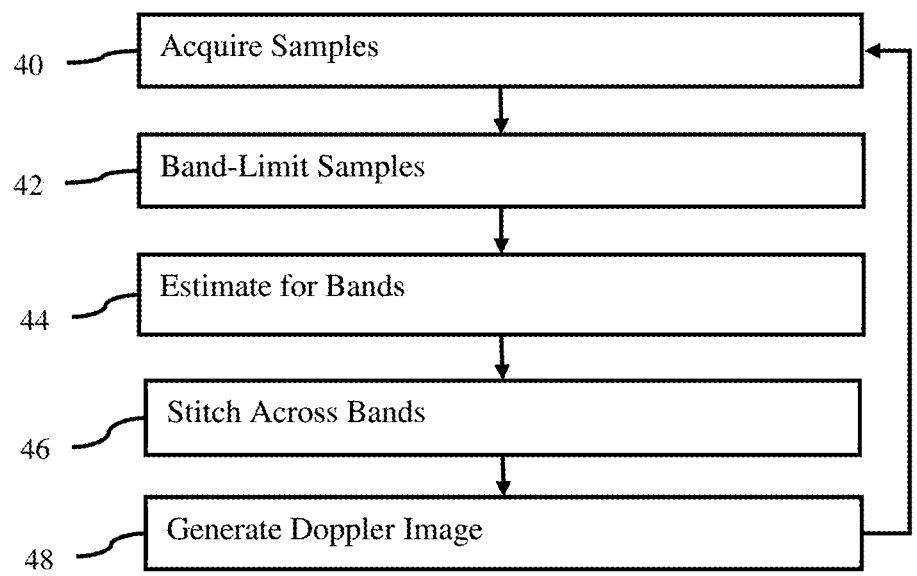
FIG. 3 is a flow chart diagram of one embodiment of a method for spectral Doppler imaging with an increased signal-to-noise ratio.

In other embodiments using both speckle reduction and signal-to-noise ratio increase, the method of FIG. 3 is used. For each group, the samples are repetitively used to separately estimate for different parts of the frequency range of the velocity scale. The partial spectrum within each group are stitched together to form the spectrum for the group. These group-specific spectra have increased signal-to-noise ratio. By combining the spectra from the different groups, the speckle may be reduced.

In alternative embodiments, all of the samples are used for both speckle reduction and for increasing the signal-to-noise ratio. The same samples are processed twice—once for increasing signal-to-noise ratio and once for speckle reduction. The spectral strips resulting from each repetition are combined, such as averaging or weighted averaging.

FIG. 3 shows a method for spectral Doppler imaging with increased signal-to-noise ratio. By band-limiting the same samples for different ranges of the velocity scale, partial spectra with increased signal-to-noise ratio are created. The partial spectra are stitched together to form a spectrum with increased signal-to-noise ratio for the entire velocity scale.

In other embodiments, the method is for color or flow mode imaging. Rather than processing by estimating spectra for different sub-bands of the velocity scale, the Doppler velocity (e.g., mean velocity) is estimated for each sub-band. The resulting velocities from the different sub-bands are averaged.

The method is implemented by the system 10 of FIG. 9 or a different system. The ultrasound system, such as a beamformer and transducer, acquire samples. A filter, such as a clutter or anti-aliasing filter, band-limits the samples. A Doppler estimator or processor estimates spectra (e.g., partial spectrum), and stitches the spectra to form a spectrum for the range gate at a given time or period. The ultrasound system displays an image with increased signal-to-noise ratio. A processor controls the acts. One or more acts may be performed through interaction with a user. Other acts or all the acts may be performed automatically by a processor without user input other than initial activation or gate location determination.

The acts are performed in the order shown, but other orders are possible. Additional, different, or fewer acts may be provided. For example, act 48 is not performed. In yet another example, acts for speckle reduction, processing, maximum velocity determination over time, or other Doppler functions are provided.

In act 40, the ultrasound system (e.g., beamformers and transducer) acquire samples representing a location of a patient. The samples at least satisfy the Nyquist criterion for the velocity scale set for the Doppler imaging. The acquisition is the same or different than discussed above for act 30 of FIG. 1. Unlike speckle reduction, oversampling is not used. In alternative embodiment, oversampling relative to the velocity scale is used.

If the system has access to the samples, then the system may reduce the bandwidth to improve the signal-to-noise ratio (SNR), as represented by $$SNR = 20 * \log_{10}\left(\sqrt{\frac{BW_{in}}{BW_{out}}}\right).$$

Reduction in bandwidth increases signal-to-noise ratio. The problem with narrowing the spectrum beyond the velocity scale is that the narrowing may cut off signals of interest. Rather than oversample and narrow to broader than or equal to the velocity scale, the narrowing may be to different ranges less than the velocity scale but representing the velocity scale in total. The samples are band-limited to less than the velocity scale in two or more sets, so the narrowing may be to ranges less than the velocity scale.

Figure 4A:
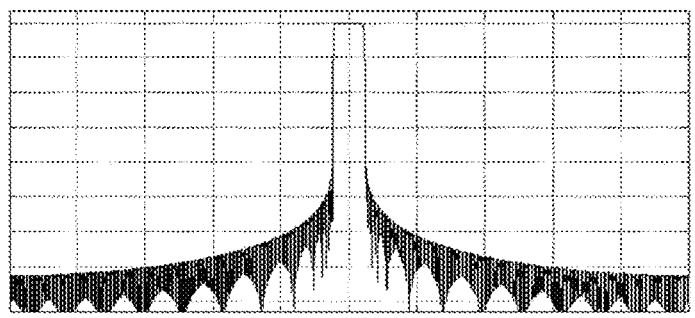
FIGS. 4A, 4C, and 4E show filter spectra for a full pass band, a first half pass band, and a second half pass band, respectively.

In act 42, the samples are filtered in different sets. The same samples are filtered two times or more, such as filtering the same starting samples with different narrow bands. In one embodiment, the samples are filtered to isolate signal in ½ the velocity scale range of frequencies (e.g., positive frequencies), and the samples are also filtered to isolate signal the other ½ of the velocity scale range of frequencies (e.g., negative frequencies). FIGS. 4A, 4C, and 4E show one example. FIG. 4A shows filter response for filtering the samples with a pass band for the entire velocity scale. The bandwidth of the velocity scale for this example is 12.5 kHz, but may be greater or lesser. FIGS. 4C and 4E show filter response for filtering the samples with negative and positive halves (i.e., $-\pi/2$ to 0 and 0 to $\pi/2$) pass bands of the velocity scale. The baseline is shifted so that the center frequency in the range is 0. The bandwidth for these examples is ½ of the 12.5 kHz.

Any division of the velocity scale may be used, such as by thirds, or fourths. The samples are processed multiple times with shifted band-passes to cover the entire velocity scale. The division provides equal sized sub-band frequency ranges. Alternatively, the size of the ranges may vary or be different, such as $-\pi/2$ to $-\pi/4$, $-\pi/4$ to $\pi/4$, and $\pi/4$ to $\pi/2$.

The sub-bands may overlap. For example, the examples of FIGS. 4C and 4E show some overlap around 0 Hz. This overlap is due to non-ideal filtering. The filter uses any number of taps in a finite impulse response, such as 128 or 256 taps. The drop at the cut-off frequency of 0 Hz may be strong, but still results in overlap. The overlap may be by design. Alternatively, the different ranges are exclusive.

In act 44, a Doppler processor estimates spectra for each of the narrow bands. The filtered samples of each band are separately used to estimate a spectrum. Since the spectrum that results is for only part of the velocity scale, the spectrum is a partial spectrum relative to the velocity scale. The filtering for the different sub-bands provides different sets of data. A partial spectrum is estimated for each of the sets. The values for different ranges of frequencies within the velocity scale are estimated from the band-limited samples. The spectral estimation is performed for each of the different ranges of the frequencies.

For color flow, the estimation is of the mean velocity. The samples output from the filtering at the different ranges are processed by mean velocity estimation rather than spectral estimation. Since the same samples are used for filtering, the estimation is a reprocessing of the samples, but at the different ranges of frequencies. Sequential or parallel processing may be used.

By reprocessing the same samples multiple times with different reduced bandwidths, the same data may be used to increase signal-to-noise ratio while still providing information across the entire velocity scale. In the spectral Doppler embodiments, the partial spectra represent exclusive or overlapping parts of the spectrum for a given time.

Figure 4B:
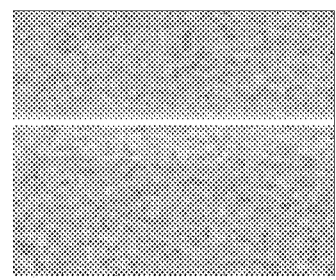
FIGS. 4B, 4D, and 4F show example displays of a tone using the respective pass bands.
Figure 4C:
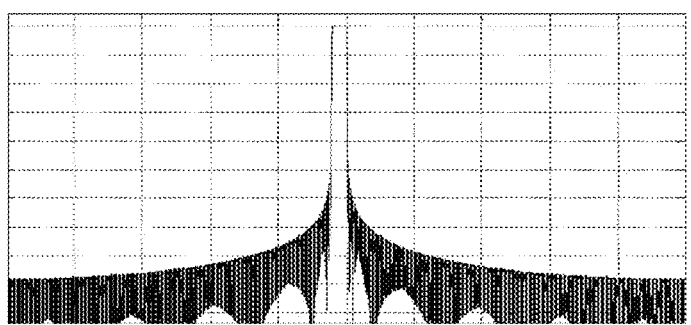
Figure 4D:
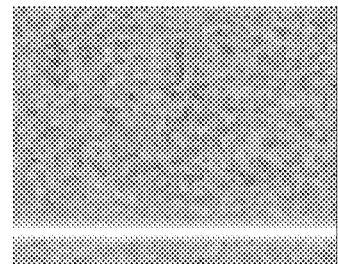
Figure 4E:
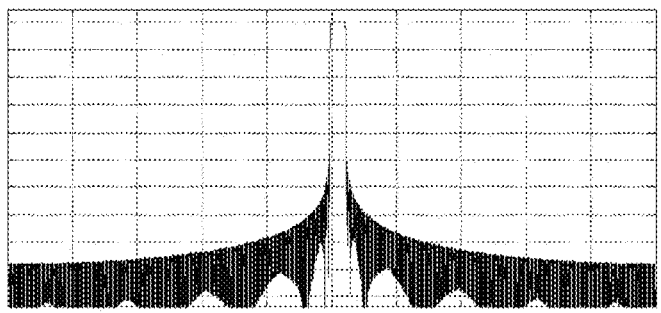
Figure 4F:
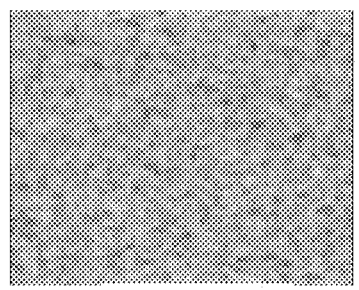

FIGS. 4B, 4D, and 4F show spectral strips from estimation performed on band-limited samples after applying the filters of FIGS. 4A, 4C, and 4E, respectively. The input signal is a tone at 5.2 kHz with added white noise sampled at 12.5 kHz. 256 samples are used for a given period or time, and the estimation is with a 256 point FFT. The range of frequencies is shifted to be 0-12.5 kHz, so the normalized baseline is at 6.25 kHz. As a result, FIG. 4B shows the tone as a white line near but negative to the base line. FIG. 4D, which band limits to the negative half of the bandwidth, shows the tone at a lower portion or near the baseline. FIG. 4E, which band limits to the positive half of the bandwidth, does not show the tone. The band-limited spectra only represent different parts of the total velocity scale.

In act 46, the values from the estimation are stitched together. For spectral Doppler, the values are the partial spectra. In the example of FIGS. 4C and 4E, the partial spectra are the positive and negative (relative to the baseline) parts of the spectrum. The partial spectrum are connected or linked to form the whole spectrum. The resulting spectrum may be low pass filtered for energy as a function of frequency. For any overlap, the energies for each overlapping frequency are averaged. The spectra estimated for the different narrow ranges are linked together across the velocity scale into a stitched spectrum, providing a stitched value for the whole velocity scale. This stitched whole represents all the frequencies of interest, such as the frequencies of the velocity scale, but with improved signal-to-noise ratio due to the band limiting.

For color or flow Doppler, the stitching is by averaging or summing. The estimated velocities at the different narrow bands are stitched together to provide a stitched value for the location. By stitching, the stitched value is responsive to the signal over the entire velocity scale.

In act 48, a Doppler image is generated. For spectral Doppler, the image is generated as discussed above for FIG. 1. A spectral strip is generated where the spectrum for a given time is added to the spectral strip. The spectrum is stitched together from the narrow band information.

For color or flow imaging, the stitched value is mapped to a color. The resulting color for that location at that time is output as a pixel value for imaging. The process is repeated for other locations to provide a color or flow image representing the patient at a given time. The process is repeated for other times to provide a sequence of color or flow images.

The process is repeated for each time or period. The feedback from act 48 to act 40 represents repetition to form the spectral strip or sequence of color or flow images.

Figure 5A:
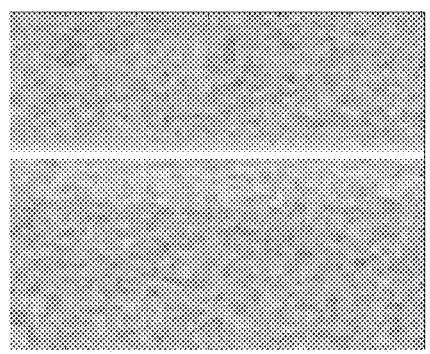
FIGS. 5A and 5B show spectral Doppler images for a tone without and with signal-to-noise ratio increase, respectively.
Figure 5B:
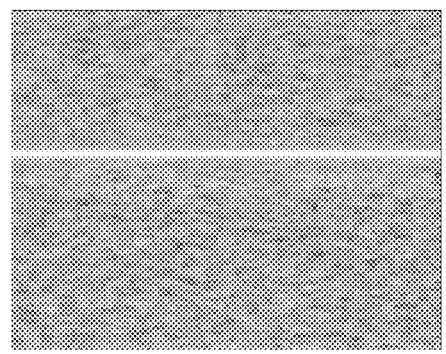
Figure 6:
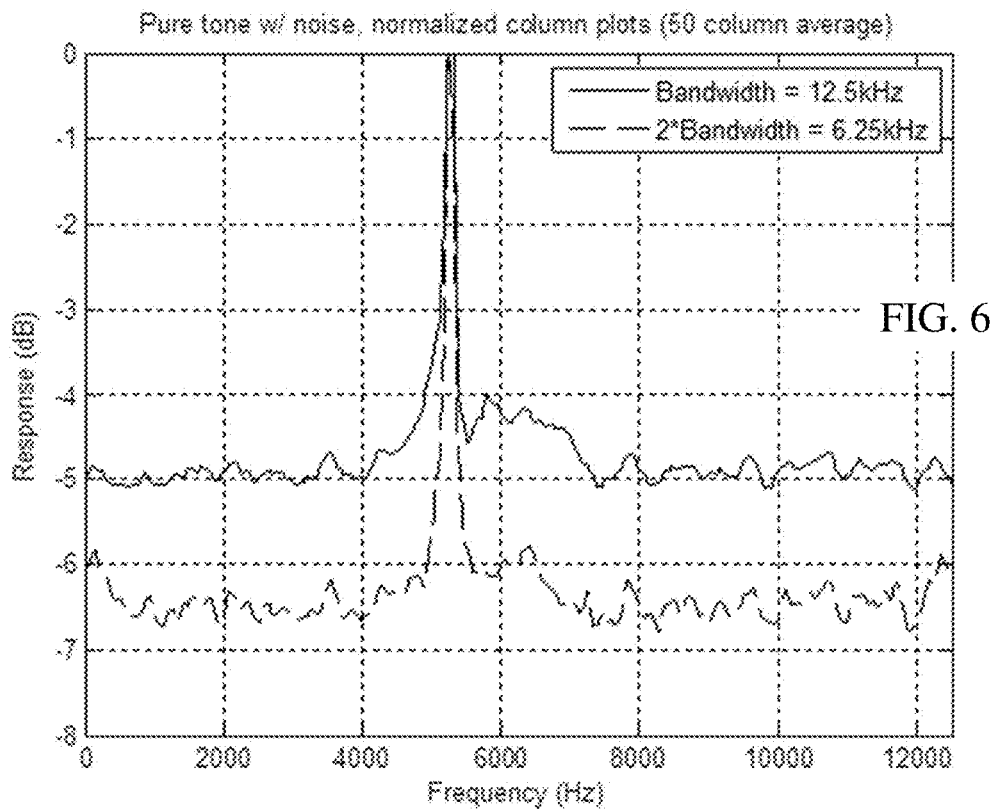
FIG. 6 shows the signal and noise as a function of frequency corresponding to FIGS. 5A and 5B.

FIGS. 5A and 5B show spectral strips. FIG. 5A shows the spectral strip generated using the filtering of FIG. 4A on the same tone and noise. FIG. 5A is the same as FIG. 4B, but enlarged. FIG. 5B shows the spectral strip resulting from the band-limiting for FIGS. 4C and 4E and stitching together of the spectra. In comparing FIGS. 5A and 5B, FIG. 5B has visibly improved signal-to-noise ratio. FIG. 6 shows a fifty column (i.e., fifty times or periods or fifty spectra) average traces of energy as a function of frequency from FIGS. 5A and 5B. The upper trace is without band-limiting (FIG. 5A), so has greater energy in the noise regions (i.e., outside of 5.2 kHz). The lower trace is with the left side/right side band-limiting (FIG. 5B), so has less energy in the noise regions. The signal-to-noise ratio is improved.

In further embodiments, the increase in signal-to-noise ratio is provided with speckle reduction as described above for FIG. 1. The samples are separated into different groups. Within each group, the signal-to-noise increase process of FIG. 3 is performed. The resulting spectra from the different groups are each stitched spectra. Information resulting from the stitched spectra estimation are combined, such as by summing or averaging stitched spectra.

In another approach, the samples are separately processed once using the process of FIG. 1 and another time using the process of FIG. 3. The resulting spectra (e.g., combined spectrum from FIG. 1 method and stitched spectrum from FIG. 3 method) are combined, either as spectra or as pixel values mapped from the spectra.

Figure 7:
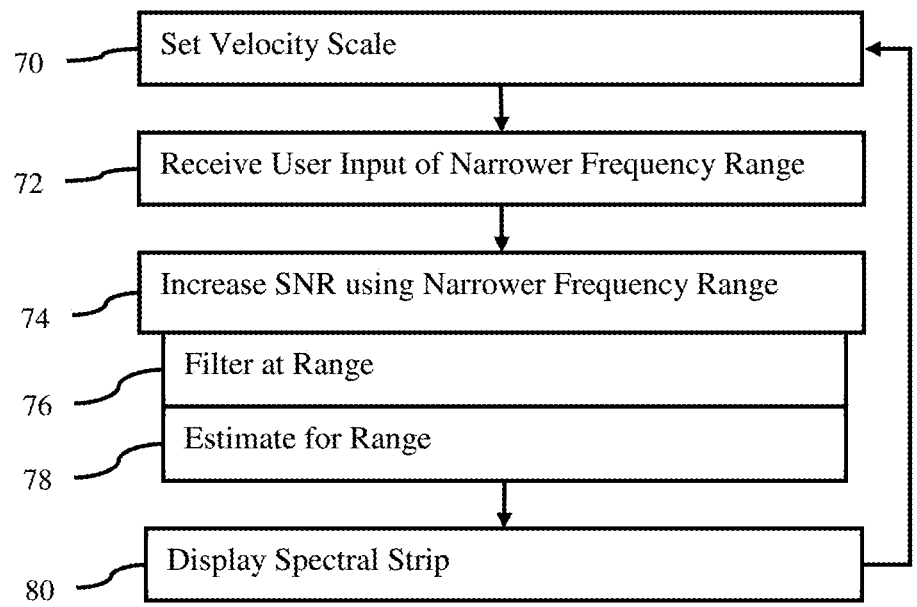
FIG. 7 is a flow chart diagram of one embodiment of a method for spectral Doppler imaging with user selected frequency band or frequency range for signal-to-noise increase.

FIG. 7 shows a method for spectral Doppler imaging with increased signal-to-noise ratio. Rather than band-limiting the same samples for different ranges of the entire velocity scale, the band limiting is performed for one or more user selected bands that are less than, even in total, all of the velocity scale.

In other embodiments, the method is for color or flow mode imaging. Rather than processing by estimating spectra for different sub-bands of the velocity scale, the Doppler velocities (e.g., mean velocities) are estimated for one or more sub-bands. The resulting velocities from the different sub-bands are displayed separately or stitched together, such as by summing or averaging.

The method is implemented by the system 10 of FIG. 9 or a different system. The ultrasound system, such as a beamformer and transducer, acquire samples. A filter, such as a clutter filter, band-limits the samples. A Doppler estimator or processor estimates spectra (e.g., partial spectrum), and stitches the spectra to form a spectrum for the range gate at a given time or period. The ultrasound system displays an image with increased signal-to-noise ratio. A processor controls the acts. One or more acts may be performed through interaction with a user. Other acts or all the acts may be performed automatically by a processor without user input other than initial activation or gate location determination.

The acts are performed in the order shown, but other orders are possible. Additional, different, or fewer acts may be provided. For example, act 80 is not performed. In yet another example, acts for speckle reduction, processing, maximum velocity determination over time, or other Doppler functions are provided.

In act 70, the velocity scale is set. The velocity scale is set by the user to avoid aliasing. In other embodiments, a default or predetermined velocity scale is used. For example, the processor sets the velocity scale in response to user selection of a particular imaging application. In yet other embodiments, samples are acquired and used to adaptively set the velocity scale by the processor. The set velocity scale provides a frequency range of interest for spectral Doppler imaging. The displayed Doppler information is for the range of frequencies for the velocity scale.

In act 72, user input of a frequency range less than the velocity scale is received. The user indicates a sub-band of the velocity scale, where the sub-band is of particular interest. The sub-band is less than and entirely within the frequency range of the velocity scale. For example, the user is interested in the maximum velocity, so selects a negative or positive range at the high end (e.g., π/2 to π/4) of the velocity scale. In alternative embodiments, the user input range extends beyond the frequency range of the velocity scale, such as where the samples are oversampled.

The filter receives the user input. The user input may be received directly from the user interface. Alternatively, the filter receives the user input as filter parameters or programming determined by a control processor based on the user input. The user may select a range or select an application corresponding to selection of the frequency range (e.g., spectral Doppler with maximum trace emphasis). The selection is of a sub-section of the spectral Doppler display for enhanced signal-to-noise ratio. For color or flow Doppler, the selection is for a range to be used in a separate or adjacent image.

In act 74, the signal-to-noise ratio is increased using the narrow frequency range or ranges selected by the user. Acts 76 and 78 represent one approach. The samples are filtered in act 76 by an anti-aliasing filter or other programmable or selectable filter with a band pass at the selected range. Separate filtering is performed for the different ranges, such as not filtering for the range of the velocity scale and filtering for a sub-band. The mean velocity or spectrum are estimated by a Doppler estimator for each of the selected ranges in act 78. The system reprocesses the samples for the selected band of the display using a reduced bandwidth to get a "cleaner" signal in the spectrum of interest.

The spectrum for the velocity scale may additionally be estimated. Any oversampling may be used to filter the samples with the velocity scale band pass. The spectrum is estimated for spectral Doppler imaging using the velocity scale.

In act 80, a Doppler image, such as a spectral strip or color flow image, is generated. The image is generated from an output (e.g., spectrum) of the estimation in the user selected, narrow band (e.g., sub-band of the velocity scale). For example, a spectral strip display is generated where the frequency range is of the narrow or user selected band. Due to the band limiting, the resulting spectral strip has increased signal-to-noise ratio as compared to a spectral strip for the entire frequency range of the velocity scale.

The image using the narrow band may be combined with an image for the entire velocity scale. For example, the portions of the spectral strip over the entire velocity scale corresponding to the narrow band are replaced with the spectral strip or information from the narrow band estimation, such as shown in FIG. 8B. The same samples are used to create a spectral strip over the entire velocity scale as well as the band limited spectral strip over a sub-portion of the velocity scale. As another example, a spectral strip for the entire velocity scale is displayed adjacent to the spectral strip for the narrow band. For color or flow Doppler, the images from estimates using the entire velocity scale and using the narrower band are displayed adjacent to each other.

To maintain a same time scale despite band limiting, a fewer number of samples are used for estimating for the narrow band. The number of samples decreases with the amount of down-sampling.

Figure 8A:
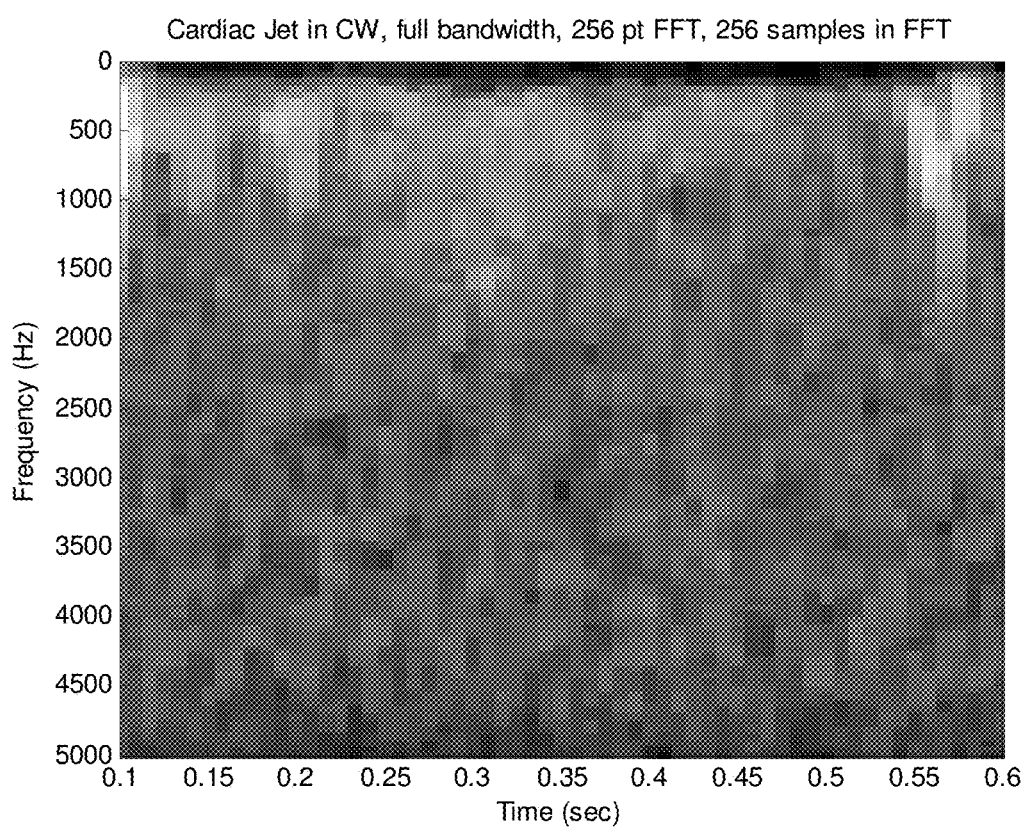
FIGS. 8A and 8B show example spectral images without and with signal-to-noise increase for a selected frequency range or band.
Figure 8B:
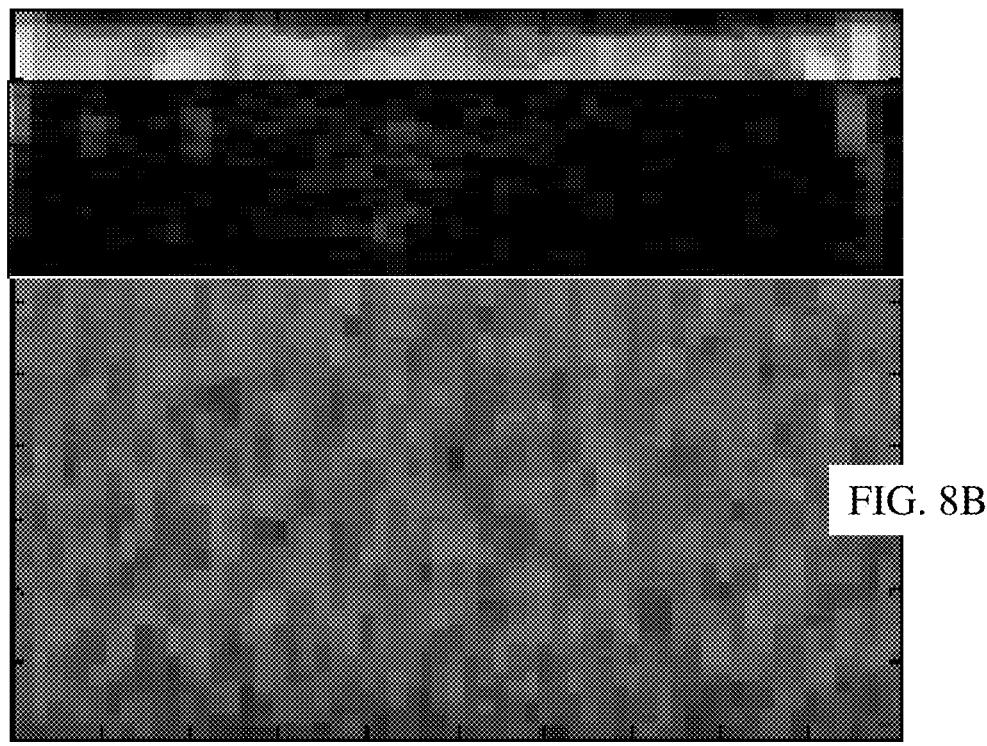

FIG. 8A shows a spectral strip for a cardiac jet in CW with full band width (e.g., 5 kHz velocity scale) with a 256 point FFT. FIG. 8B shows the same spectral strip as FIG. 8A, but having improved (less white noise) signal-to-noise ratio for the 500-1800 Hz band. The spectra estimated for the narrower band after filtering are overlaid or replace the parts of the spectra estimated for the entire velocity scale.

FIG. 9 shows a system 10 for spectral or color Doppler imaging. The system 10 is a medical diagnostic ultrasound imaging system, but other imaging systems may be used, such as a workstation. The system 10 acquires responses at one or more locations at a high rate, sampling response from each location for estimating velocity, such as estimating spectra or mean velocity.

The system 10 includes a transmit beamformer 12, a transducer 14, a receive beamformer 16, a Doppler processor 18, a display 20, a processor 21, and a memory 22. Additional, different or fewer components may be provided, such as the system 10 without the front-end beamformers 12, 16 and transducer 14 or the system 10 with a scan converter. The Doppler processor 18 and processor 21 may be combined into one device acting as both processors 18, 21, or additional processors for sequential or parallel processing may be used.

The transducer 14 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, combinations thereof, or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit beamformer 12 is shown separate from the receive beamformer 16. Alternatively, the transmit and receive beamformers 12, 16 may be provided with some components in common. Operating together or alone, the transmit and receive beamformers 12, 16 form beams of acoustic energy for sampling a gate location and/or scanning a one, two, or three-dimensional region.

The transmit beamformer 12 is a processor, delay, filter, waveform generator, memory, phase rotator, digital-to-analog converter, amplifier, combinations thereof, or any other now known or later developed transmit beamformer components. In one embodiment, the transmit beamformer 12 digitally generates transmit waveform envelope samples. Using filtering, delays, phase rotation, digital-to-analog conversion and amplification, the desired transmit waveform is generated. In other embodiments, the transmit beamformer 12 includes switching pulsers or waveform memories storing the waveforms to be transmitted. Other transmit beamformers 12 may be used.

The transmit beamformer 12 is configured as a plurality of channels for generating electrical signals of a transmit waveform for each element of a transmit aperture on the transducer 14. The waveforms are unipolar, bipolar, stepped, sinusoidal, or other waveforms of a desired center frequency or frequency band with one, multiple, or fractional number of cycles. Alternatively, the transmit beamformer 12 generates continuous waves for CW imaging. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles, coding, or combinations thereof.

The transmit beamformer 12 is configured to transmit a sequence of transmit beams of ultrasound energy. A transmit beam originates from the transducer 14 at a location in the transmit aperture. The transmit beam is formed along a scan line at any desired angle. The acoustic energy is focused at a point along the scan line, but multiple points, line focus, no focus, or other spread may be used. The acoustic energy is focused at the Doppler gate location, but may be focused elsewhere (e.g., the Doppler gate is along the scan line but not at the focus). The beam of acoustic energy is transmitted to the Doppler gate or to other locations.

For each location, an ongoing sequence of transmit beams are generated at a PRF. The PRF determines the interval between temporally adjacent transmissions or transmit beams. The PRF may be low enough to have a period of no transmission not needed for travel time, interleaving with other imaging modes, and reverberation reduction. In one embodiment, the PRF is as rapid as possible given the travel time, interleaving, and reverberation reduction of ½ the travel time or less. A higher PRF more likely provides oversampling. In other embodiments, the PRF is set based on the velocity scale and the Nyquist criterion.

The receive beamformer 16 is a preamplifier, filter, phase rotator, delay, summer, base band filter, processor, buffers, memory, combinations thereof, or other now known or later developed receive beamformer component. Analog or digital receive beamformers capable of receiving one or more beams in response to a transmit event may be used.

The receive beamformer 16 is configured into a plurality of channels for receiving electrical signals representing echoes or acoustic energy impinging on the elements of the transducer 14. A channel from each of the elements of the receive aperture within the transducer 14 connects to an amplifier for applying apodization amplification. An analog-to-digital converter may digitize the amplified echo signal. The radio frequency received data is demodulated to a base band frequency. Any receive delays, such as dynamic receive delays, and/or phase rotations are then applied by the amplifier and/or delay. A digital or analog summer combines data from different channels of the receive aperture to form one or a plurality of receive beams. The summer is a single summer or cascaded summers. The summer sums the relatively delayed and apodized channel information together to form a receive beam. Beamformed samples of echoes from the one or more locations are obtained (e.g., from one gate location for spectral Doppler or from multiple locations for color or flow imaging).

In one embodiment, the beamform summer is operable to sum in-phase and quadrature channel data in a complex manner such that phase information is maintained for the formed beam. Alternatively, the beamform summer sums data amplitudes or intensities without maintaining the phase information. Other receive beamformation may be provided, such as with demodulation to an intermediate frequency band and/or analog-to-digital conversion at a different part of the channel.

Beamforming parameters including a receive aperture (e.g., the number of elements and which elements used for receive processing), the apodization profile, a delay profile, a phase profile, imaging frequency, inverse coding, or combinations thereof are applied to the receive signals for receive beamforming. For example, relative delays and amplitudes or apodization focus the acoustic energy along one or more scan lines. A control processor controls the various beamforming parameters for receive beamformation.

One or more receive beams are generated in response to each transmit beam. Acoustic echoes are received by the transducer 14 in response to the transmitted acoustic energy. The echoes are converted into electrical signals by the transducer 14, and the receive beamformer 16 forms the receive beams from the electrical signals to generate samples representing the location or locations. Given the ongoing transmit beams at the PRF for each location, samples are generated in an ongoing manner as well. Responses over time are acquired.

The Doppler processor 18 is a spectral Doppler estimator or a color or flow Doppler estimator. Other imaging detectors may be included, such as a B-mode. In one embodiment, the Doppler processor 18 is a digital signal processor or other device for applying a transform to the receive beam sample data. A sequence of transmit and receive events is performed over a period. A buffer (e.g., corner turning memory) or the memory 22 stores the receive beamformed data from each transmit and receive event. A wall filter, such as a programmable filter for distinguishing between tissue and fluid motion, may filter the samples prior to application of the transform. An anti-aliasing filter separate from or implemented by the wall filter may down sample the data for increasing signal-to-noise ratio. Any number of transmit and receive events may be used for determining a spectrum, such as three or more. The Doppler processor 18 estimates a spectrum for the gate location or estimates a mean velocity. By applying a discrete or fast Fourier transform, or other transform to the ultrasound samples for the same spatial location, the spectrum representing the response from the location is determined. A histogram or data representing the energy level at different frequencies for the period to acquire the samples is obtained. Velocity may be determined from the frequency or frequency is used without conversion to velocity.

By repeating the process, the Doppler processor 18 may obtain different spectra for a given location at different times. Overlapping data may be used, such as calculating each spectrum with a moving window of selected ultrasound samples. Alternatively, each ultrasound sample is used for a single period and corresponding spectrum. By repeating for different locations, a spatial distribution of mean velocities may be estimated.

The Doppler processor 18 applies the transform for a range of frequencies. The range of frequencies or velocity scale limits the positive and negative velocities resulting from the estimation. Any of various velocity scales may be used, up to and including a velocity scale equal to the transmission PRF. The spectra are estimated using a given velocity scale. Similarly, the baseline or center of the velocity scale may be set.

The Doppler processor 18 may reduce speckle or other noise by separating oversampled samples into different groups for separate estimation and then combination of information resulting from the separate estimation. The Doppler processor 18 may increase signal-to-noise ratio by processing the samples multiple times for bands narrower than the range of frequencies of the velocity scale and stitching together the results. The Doppler processor 18 may provide estimates at a greater signal-to-noise ratio for a sub-band of the band of the velocity scale by estimating from signals of the sub-band alone. Combinations of any two or all of these approaches may be used.

The processor 21 may be part of the Doppler processor 18 or a separate processor. The processor 21, Doppler processor 18, or both processors 18, 21 are used for sample selection or distribution, estimation and/or to control the imaging and/or system 10. The processor 21 is a general processor, control processor, digital signal processor, application specific integrated circuit, field programmable gate array, graphics processing unit, analog circuit, digital circuit, combinations thereof or other now known or later developed device for processing.

The processor 21 is configured by hardware, software, or both to perform and/or cause performance of various acts, such as the acts discussed above for FIGS. 1, 3 and/or 7. The processor 21 is configured, as part of or in communication with the Doppler processor 18. The processor 21 sets the PRF for the beamformers 12, 16 given a location of a Doppler gate relative to the transducer 14. The processor 21 generates or causes the Doppler processor 18 to generate the spectral strip. As the acquisition and estimation continue, spectra are added to the strip and old spectra are removed in a first-in, first-out scroll.

The processor 21 operates automatically. The user activates the spectral Doppler mode, indicates a velocity scale, indicates a baseline, and/or may position the gate. The speckle reduction and/or signal-to-noise ratio increase are performed without further user input and/or without user input of values for one or more of the Doppler imaging parameters. In alternative embodiments, the user inputs the setting of the parameter, such as inputting a band narrower than the velocity scale. The processor 21 causes estimation of the spectra over time.

Additional processes, such as filtering, interpolation, and/or scan conversion, may be provided by the Doppler processor 18, the processor 21, or another device. The spectra are prepared and formatted for display. For example, the Doppler processor 18 generates display values as a function of the spectra estimated for the locations. Display values include intensity or other values to be converted for display (e.g., red, green, blue values) or analog values generated to operate the display 20. The display values may indicate intensity, hue, color, brightness, or other pixel characteristic. For example, the color is assigned as a function of one characteristic of a spectrum and the brightness is a function of another spectrum characteristic or other information. The display values are generated for a spectral strip display.

The display 18 is a CRT, monitor, LCD, plasma screen, projector or other now known or later developed display for displaying an image responsive to the spectra. For a grey scale spectral Doppler image, a range of velocities with each velocity modulated as a function of energy is provided as a function of time. A given spectrum indicates the velocity and energy information for a given time. The intensity of a given pixel or pixel region represents energy where velocity is provided on the vertical scale and time provided on the horizontal scale. Other image configurations may be provided, including colorized spectral Doppler images. A color or flow mode image may be generated, such as showing mean velocity as a function of location in a region of interest in a grayscale B-mode.

The memory 22 stores ultrasound samples for the location or locations, estimated spectra, partial spectra, settings (e.g., values) for parameters, image data, or other information. The memory 22 may store information from any stage of processing or used for generating a display.

In one embodiment, the memory 22 is a non-transitory computer readable storage medium having stored therein data representing instructions executable by the programmed processor 18 and/or processor 21 for Doppler imaging. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts, or tasks are independent of the particular type of instructions set, storage media, processor, or processing strategy and may be performed by software, hardware, integrated circuits, firmware, micro code or the like, operating alone or in combination. Likewise, processing strategies may include multiprocessing, multitasking, parallel processing and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for spectral Doppler imaging, the method comprising:
    acquiring, with an ultrasound system, samples representing a range gate location, the samples oversampled relative to a velocity scale set for the spectral Doppler imaging;
    separating the samples into two or more groups with each group of the samples satisfying a Nyquist criterion for the velocity scale;
    estimating, by a Doppler estimator, two or more spectra for the Doppler gate location from the samples of the two or more groups, respectively;
    combining information for the two or more spectra into a combined spectrum; and
    displaying a spectral Doppler strip as a function of the combined spectrum.

2. The method of claim 1 wherein acquiring comprises transmitting with a pulse repetition frequency for oversampling.

3. The method of claim 1 wherein acquiring comprises acquiring with the samples as oversampled by M times the Nyquist criterion for the velocity scale, where M is an integer, and wherein separating into the two or more groups comprises separating into M groups.

4. The method of claim 1 wherein separating the samples comprises separating the samples into the two or more groups with each group having independent noise.

5. The method of claim 1 wherein separating the samples comprises interleaving the samples into the two or more groups such that each sample is only in one group prior to any filtering across the samples.

6. The method of claim 1 wherein estimating comprises applying a Fourier transform to the samples, the two or more spectra each comprising energy as a function of frequency over a range set by the velocity scale.

7. The method of claim 1 wherein combining comprises summing the two or more spectra.

8. The method of claim 1 wherein displaying comprises displaying the spectral Doppler strip with the combined spectrum representing a time.

9. The method of claim 1 further comprising repeating the acquiring, separating, estimating, and combining for different times, and wherein displaying comprises displaying the spectral Doppler strip with each of the combined spectra representing different times.

10. The method of claim 1 further comprising increasing signal-to-noise ratio of the spectral Doppler strip with downsampling of the samples.

11. The method of claim 1 further comprising:
    band-limiting the samples to less than the velocity scale in two or more sets;
    estimating two or more spectra for the two or more sets;
    stitching the two or more spectra together into a stitched spectrum; and
    combining the stitched spectrum with the combined spectrum.

12. The method of claim 1 further comprising:
    receiving user input of a frequency range less than the velocity scale; and
    increasing signal-to-noise ratio using the frequency range.

* * * * *